US008835676B2

(12) United States Patent
Divi et al.

(10) Patent No.: US 8,835,676 B2
(45) Date of Patent: Sep. 16, 2014

(54) **PROCESS FOR THE PREPARATION OF ENANTIOMERICALLY PURE *TERT*-LEUCINE**

(75) Inventors: Murali Krishna Prasad Divi, Hyderabad (IN); Gundu Rao Padakandla, Hyderabad (IN); Mysore Aswatha Narayana Rao, Hyderabad (IN); Shaik Nowshuddin, Hyderabad (IN)

(73) Assignee: Divi's Laboratories Ltd. (IN)

( * ) Notice: Subject to any disclaimer, the term of this patent is extended or adjusted under 35 U.S.C. 154(b) by 762 days.

(21) Appl. No.: 13/154,612

(22) Filed: Jun. 7, 2011

(65) Prior Publication Data

US 2012/0245379 A1    Sep. 27, 2012

(30) Foreign Application Priority Data

Mar. 21, 2011  (IN) .......................... 0856/CHE/2011

(51) Int. Cl.
*C07B 57/00* (2006.01)
*C07C 227/34* (2006.01)
*C07C 67/52* (2006.01)
*C07C 67/28* (2006.01)

(52) U.S. Cl.
CPC ............... *C07C 227/34* (2013.01); *C07C 67/52* (2013.01); *C07B 2200/07* (2013.01); *C07C 67/28* (2013.01)
USPC ...................................................... 562/402

(58) Field of Classification Search
CPC .............................. C07B 63/00; C07C 51/487
USPC ...................................................... 562/402
See application file for complete search history.

(56) References Cited

U.S. PATENT DOCUMENTS

| | | |
|---|---|---|
| 5,219,731 A | 6/1993 | Sih |
| 6,180,374 B1 | 1/2001 | Turner et al. |
| 7,071,356 B1 | 7/2006 | Nigam et al. |
| 2010/0028959 A1 | 2/2010 | Kanamaru et al. |

FOREIGN PATENT DOCUMENTS

CN   101100436 A   *   1/2008

OTHER PUBLICATIONS

Viret et al., Tetrahedron Letters, 27(48), 5865-5868 (1986).*
Jaeger et al., J. Amer. Chem. Soc., 101(3), 717-732 (1979).*
David A. Jaeger, et al. Electrophilic Substitution at Saturated Carbon. 52, A Model for the proton Transfer Steps of Biological Transamination and the Effect of a 4-Pyridyl Group on the Base-Catalyzed Racemization of a Carbon Acid 0002-7863/79/1501-071, J. Amer, Chem Soc. 101:3 , 717-732, 1979.
Nobuo Izumiya, et al. Optical Enantiomorphs of Tertiary Leucine, (From the National Cancer Institute, National Institutes of Health, Bethesda, Maryland), (1953).
Toshifumi Miyazawa, et al. Studies on Unusual Amino Acids and their Peptides, X. The Convenient Synthesis of t-Leucine and the Optical Resolution of the N-Benzyloxycarbonyl Derivative, Bulletin of the Chemical Society of Japan, vol. 52(5), 1539-1540 (1979).
Joelle Viret, et al. Simple Optical Resolution of Terleucine, Chimie des Interactions Moleculaires, E.R. C.N.R.S. 285, College de France 11, place Marcelin-Berthelot, Paris France, 1986, 5865-5868.
Extended Search Report dated May 14, 2012.
H.Pracejus et al. Uber Optisch Aktives Tert-Leucin Und Pinacoylamin, Praceus and Winter, vol. 97, No. 11, 1964, pp. 3173-3182 and translation.
N.Oi, et al. Enantiomer Separation by HPLC on Reversed Phase Silica Gel Coated With Copper (II) complexes of (R,R)-Tartaric Acid Mono-Amide Derivatives, Journal of Liquid Chromatography, 16(4), 893-901 (1993).
Tanabe, T, et al. Syntheses of 3,3-Dimethl-2-hydroxybutyric Acid and tertiary Leucine and Their Optical Resolutions, Bulletin of the chemical Society of Japan, Chemical Society of Japan, vol. 41, No. 9, 2178-2179, (1968).
DataBase WPI, Week 199346, Thomson Scientific, London, GB, Oct. 19, 1993.
Japan patent No. JP5271169 and Abstract date Oct. 19, 1993.

* cited by examiner

*Primary Examiner* — Sudhakar Katakam
*Assistant Examiner* — Kofi Adzamli
(74) *Attorney, Agent, or Firm* — Caesar, Rivise, Bernstein, Cohen & Pokotilow, Ltd.

(57) ABSTRACT

Enantiomerically pure L-tert-leucine and D-tert-leucine were prepared from (DL)-tert-leucine by diastereomeric salt formation using dibenzoyl-d-tartaric acid as the resolving agent.

13 Claims, No Drawings

PROCESS FOR THE PREPARATION OF ENANTIOMERICALLY PURE *TERT*-LEUCINE

CROSS-REFERENCE TO RELATED APPLICATIONS

This application claims priority from India Application Serial No. 0856/CHE/2011, filed on Mar. 21, 2011, entitled A PROCESS FOR THE PREPARATION OF ENANTIOMERICALLY PURE tert-LEUCINE which application is assigned to the same assignee as this application and whose disclosure is incorporated by reference herein.

FIELD OF THE INVENTION

The present invention discloses a process for the preparation of enantiomerically pure L- and D-tert-leucines, which are nonpeptide amino acids but are widely used as chiral auxiliaries and in preparing various biologically active molecules.

BACKGROUND OF THE INVENTION

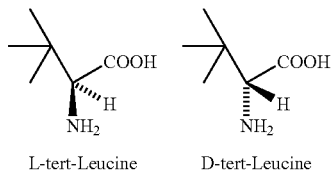

L-tert-Leucine    D-tert-Leucine

Preparation of enantiomerically pure tert-leucine has remained a major challenge in process chemistry. It was obtained by the resolution of N-tosyl-DL-tert-leucine using brucine (Jaeger, D. A., et al., *J. Am. Chem. Soc.,* 101, 717, 1979). Similarly racemic N-benzyloxycarbonyl-tert-leucine was resolved through its quinine salt (Miyazawa, T., et al., *Bull. Chem. Soc. Jpn.* 52, 1539, 1979). Ethyl ester of DL-tert-leucine has been resolved by crystallization of its dibenzoyl-d-tartrate salts (Jaeger, D. A., et al., ibid). Several enzymatic methods have also been reported. Hog kidney amidase was used to resolve DL-tert-leucine amide (Izumiya, N., et al., *J. Biol. Chem.* 205, 221-230, 1953). U.S. Pat. No. 5,219,731 describes a process where enzymatic hydrolysis of oxazolone derivative gives optically active L-tert-leucine. A similar process is reported in U.S. Pat. No. 6,180,374 using enzymatic conversion of azalactone to give chiral N-acyl derivative, which on hydrolysis results in L-tert-leucine. U.S. Patent Application 20100028959 describes a method for L-tert-leucine preparation by reductive amination of a corresponding keto compound using amino acid dehydrogenase. Direct resolution of DL-tert-leucine without any derivatization has been reported using camphor-10-sulphonic acid (Viret, J., et al., *Tetrahedron Lett.* 27, 5865-5868, 1986) where L-tert-leucine was obtained in about 23% yields after three recrystallizations requiring about three days. The general approach for the preparation of enantiomerically pure tert-leucine was to prepare either an ester or an amide of (DL)-tert-leucine and resolve using either enzymatic hydrolysis or by preparing salt of chiral acid or a base, followed by hydrolysis. We found this approach to be uneconomical.

The L-tert-leucine dibenzoyl-d-tartrate salt obtained during resolution has to be hydrolyzed using hydrochloric or sulphuric acid. This results in the formation of an acid salt. It is very difficult to obtain free tert-leucine from its salts because both tert-leucine and its acid salt are highly soluble in water.

Thus the methods described in the prior art are not satisfactory for industrial production. There is a need for an improved process which is simple, economical and gives both L- and D-isomers in high yields and purity. Both the isomers find application in drug design and discovery of new molecules.

SUMMARY OF THE INVENTION

Our principal objective was to explore direct resolution of DL-tert-leucine, without preparing any derivatives such as amide, ester etc. to obtain both D- and L-tert-leucines in pure form. We found surprisingly that dibenzyol-d-tartaric acid formed salt selectively with L-tert-leucine, which on hydrolysis gave pure L-tert-leucine. From the filtrate D-pure tert-leucine was also obtained.

Another aspect of the invention are methods to obtain pure tert-leucine free from its inorganic acid salts. We have found that L-tert-leucine HCl salt can be converted to free tert-leucine by treating the HCl salt with a non-basic acid scavengers such as epoxides. Similarly L-tert-leucine sulphate can be converted to free L-tert-leucine by treating the sulphate salt with barium hydroxide.

The invention also includes a racemisation process to recycle D-tert-leucine into DL-tert-leucine. This comes in handy when the D-tert-leucine is not directly useful for some application.

DETAILED DESCRIPTION OF THE INVENTION

The present invention provides a process for the preparation of enantiomerically pure L-tert-leucine and D-tert-leucine, which comprises:
i) dissolving (DL)-tert-leucine in a polar solvent and treating it with an optically active tartaric acid derivative,
ii) filtering the formed diastereomeric tartrate salt,
iii) hydrolyzing the diastereomeric tartrate salt with an acid,
iv) neutralizing the acid salt to obtain L-tert-leucine, and
v) isolating D-tert-leucine from the filtrate from step (ii).

DL-tert-Leucine was prepared essentially by the method of Jaeger et al. (*J. Am. Chem. Soc.* 101, 717-732, 1979). It was dissolved in a suitable polar solvent. We selected water as the solvent because of the high solubility of tert-leucine, apart from its inexpensive and environmentally friendly nature. The aqueous solution was treated with various chiral acids and bases to obtain diastereomeric salt which is selective either to L- or D-tert-leucine. We found that dibenzoyl-d-tartaric acid selectively formed a salt with L-tert-leucine, and the diastereomeric salt precipitated out because of its poor solubility in water. Best yields and chiral purity were obtained when 0.5 equivalent of resolving agent was used. Lesser amounts resulted in decreased yields. When more than 0.5 equivalents were used, there was no significant change in the yields and chiral purity of L-tert-leucine. This shows that only L-tert-leucine selectively formed salt with dibenzoyl-d-tartaric acid.

The diastereomeric L-tert-leucine dibenzoyl-d-tartrate salt can be hydrolyzed by treating with either acid or a base. When base was used, isolation of both L-tert-leucine and dibenzoyl-d-tartaric acid was difficult as they formed soluble salts. Hence, acid hydrolysis was attempted. When sulphuric acid was used for the hydrolysis of the salt, dibenzoyl-d-tartaric acid precipitated out quantitively. The L-tert-leucine sulphate remained in solution. Recovering L-tert-leucine from its sulphate salt was found to be very problematic. When a common base such as sodium hydroxide or sodium carbonate was used to hydrolyze the sulphate salt, the L-tert-leucine obtained was always found to be contaminated with significant amount of sodium sulphate. Ion exchange resin was not preferred to remove the salts because it adds to the operations and cost and may not be viable on an industrial scale. Hence we selected barium hydroxide as a base for hydrolysis because of the poor solubility of barium sulphate in water. When the aqueous solution of L-tert-leucine sulphate was carefully treated with barium hydroxide, barium sulphate precipitated out leaving pure L-tert-leucine in the solution. The solvent was removed under reduced pressure, the residue obtained was stirred with small amount of acetone to obtain colorless shining solid completely free from any sulphate. The isolated L-tert-leucine showed 99.9% chiral purity and 99.9% chemical purity with 85% yield.

The L-tert-leucine dibenzoyl-d-tartrate salt can also be hydrolyzed using dilute hydrochloric acid. Here also, dibenzoyl-d-tartaric acid precipitated out quantitatively and the HCl salt of L-tert-leucine remained in solution. However it was also difficult to obtain pure L-tert-leucine from the HCl salt by neutralization with bases such as NaOH, because the chloride salt of the bases were also soluble in water and methanol. Hence another strategy was adopted to obtain pure L-tert-leucine from its HCl salt. The epoxides such as ethylene oxide, propylene oxide, 1,2-epoxybutane are known to act as non-basic acid scavengers by reacting with HCl salts (U.S. Pat. No. 7,071,356). After exploring various epoxides, we selected easily available epichlorohydrin as the acid scavenger. The HCl salt of L-tert-leucine was stirred with epichlorohydrin in acetone. Epichlorohydrin reacts with L-tert-leucine HCl salt and is converted to 1,3-dichloropropanol which remain in acetone. The liberated L-tert-leucine is insoluble in acetone and precipitates out. On filtration, L-tert-leucine is obtained as a solid in pure form (74% yield, 99.9% chiral purity and 99.9% chemical purity). It is important to stop the reaction when the pH becomes neutral. Stirring for longer time results in impurities because of the reaction between tert-leucine and dichloropropanol.

The filtrate obtained at dibenzoyl-d-tartrate salt stage (step.ii), was treated with a small amount of diisopropyl ether to remove any traces of dibenzoyl-d-tartaric acid and was concentrated under reduced pressure at 55° C. The residue obtained was stirred with small amount of acetone and filtered to obtain D-tert-leucine as a colorless solid (90% yield, 98.8% D-tert-leucine and 1.2% L-tert-leucine).

A process was developed to racemize D-tert-leucine so that it can be recycled. Use of acids, although caused racemization, resulted in salt formation. It was tedious to obtain free amino acid from such salts. The same drawback was observed when a strong base such as sodium hydroxide was used. However, treating D-tert-leucine with ammonium hydroxide resulted in complete racemization. The reaction has to be conducted at about 80° C. for about 12 hours in an autoclave to prevent the escape of ammonia. The solvent is removed at 55° C. (±5) under reduced pressure to obtain DL-tert-leucine. After the reaction, although ammonium salt of DL-tent-leucine is obtained, during the removal of the solvent, ammonia also is eliminated and free amino acid is obtained.

The advantage of the present process over the prior art is that it gives enantiomerically pure tert-leucine directly from (DL)-tert-leucine without the need for making derivatives such as an ester or an amide. The present process is not based on any enzyme hydrolysis which is usually expensive. The process uses dibenzoyl-d-tartrate as the resolving agent which is recovered almost quantitatively because its solubility is different from that of tert-leucine in water.

In another embodiment, the present invention provides a process for obtaining free L-tert-leucine from its sulphate salt by using barium hydroxide and from its HCl salt using epichlorohydrin, a non-basic acid scavenger.

In yet another embodiment, the present invention also provides a process for the isolation and recovery of substantially pure D-tert-leucine, which may find direct application. In yet another embodiment, the present process also provides a method of racemization of D-tert-leucine as a value addition, in case the D-tert-leucine cannot find an application.

The embodiments of the present invention are illustrated in the following examples, which are not intended in any way to limit the scope of the invention. One skilled in the art can easily modify the details to suit the inputs and desired outcomes without affecting the present invention.

EXAMPLES

Chemical purity of the isolated L-tert-leucine and D-tert-leucine was determined using HPLC under the following conditions:
Column: Xterra RP 18, 250×4.6 mm, 5μ
Mobile phase: water: methanol: acetic acid (60:40:0.1), Flow rate: 0.7 mL/min.
Column Temperature: 30° C.
Detector: Shimadzu. RID-10A Enantiomeric purity of the isolated L-tert-leucine and D-tert-leucine was determined as their benzyloxycarbonyl derivatives using HPLC under the following conditions:
Column: Chiral pak AS-H 250×4.6 mm, 5μ
Mobile phase: n-hexane: IPA: TFA (50:50:0.1), Flow rate: 0.5 mL/min.
Column Temperature: 27° C.
Detector: Shimadzu. SPD-10 AVP (UV detector, 254 nm)

Example 1

(DL)-tert-Leucine (15 g, 0.1145 mol) was dissolved in water (180 mL). To the solution was added dibenzoyl-d-tartaric acid monohydrate (21.5 g, 0.057 mol) and stirred for 24 hours at 28° C. (±3). The reaction mixture was filtered to collect L-tert-leucine dibenzoyl-d-tartrate salt. The filtrate was reserved for isolating D-tert-leucine later. The tartrate salt was added to water (150 mL) followed by concentrated sulphuric acid (3 mL) and stirred for 4 hours. Liberated dibenzoyl-d-tartaric acid was collected and dried (19.8 g, 92% yield). The filtrate was washed with diisopropyl ether (50 mL) to remove any traces of dibenzoyl-d-tartaric acid, cooled to 5° C. and treated with a saturated solution of barium hydroxide till the pH was neutral. It was filtered to remove the precipitated barium sulphate. The filtrate was concentrated under reduced pressure to remove all the solvent. The residue obtained was stirred with acetone (15 mL×2), filtered and dried to obtain colorless solid L-tert-leucine (6 g, 80% yield, 99% chemical purity, 99.9% chiral purity).

The filtrate obtained after removing L-tert-leucine dibenzoyl-d-tartrate salt was concentrated under reduced pressure. The residue obtained was stirred with acetone (15 mL×2), filtered and dried to obtain colorless solid of D-tert-leucine (6.37 g, 85% yield, 98.5% chemical purity, 98% chiral purity).

Example 2

A mixture of L-tert-leucine.dibenzoyl-d-tartrate salt (27 g) as obtained in example-1, water (150 mL) and concentrated hydrochloric acid (50 mL) was stirred for 12 hours. The liberated dibenzoyl-d-tartaric acid was filtered and dried (20 g). The filtrate was concentrated under reduced pressure to remove all the solvent. The residue obtained was stirred with acetone (15 ml×2), filtered and dried to obtain colorless solid of L-tert-leucine hydrochloride salt. It was suspended in toluene (50 mL) and epichlorohydrin (5.8 g) was added. The reaction mixture was stirred till the pH was neutral. It was filtered, the solid obtained was stirred with acetone (15 ml×2) and again filtered to obtain L-tert-leucine (5.6 g, 75% yield, 98.5% chemical purity, 99.9% chiral purity).

Example 3

Ammonium hydroxide (50 mL, 30%) solution was placed in an autoclave and D-tert-leucine (5 g) was added. Autoclave was closed and the contents were heated to 85° C. under stirring for 12 hours. After cooling the solution was transferred and concentrated under vacuum at 55° C. The solid residue obtained was stirred with acetone (20 mL), filtered and dried to obtain DL-tert-leucine (4.6 g, 92% yield, L-isomer: 42%, D-isomer: 58%)

We claim:

1. A process for the preparation of enantiomerically pure tertiary-leucine which is L-tert-leucine by resolution of (DL)-tertiary-leucine by forming a diastereomeric salt using a resolving agent selected from optically active tartaric acid derivatives, comprising:
   (a) dissolving (DL)-tent-leucine in a polar solvent and treating it with dibenzoyl-d-tartaric acid to create a suspension,
   (b) filtering the suspension to obtain selectively L-tert-leucine dibenzoyl-d-tartrate salt,
   (c) treating the tartrate salt with an acid to obtain an acid salt of L-tert-leucine and free dibenzoyl-d-tartaric acid, and
   (d) neutralizing the acid salt to obtain free L-tert-leucine.

2. The process according to claim 1 step (c), wherein the acid used is sulphuric acid and the salt obtained is the sulphate salt.

3. The process according to claim 2, wherein the sulphate salt is neutralized using a barium compound to obtain free L-tert-leucine.

4. The process according to claim 1 step (c), wherein the acid used is hydrochloric acid and the salt obtained is the hydrochloride salt.

5. The process according to claim 4, wherein the hydrochloride salt is neutralized using a non-basic acid scavenger to obtain L-tert-leucine.

6. The process according to claim 1(b), wherein the filtrate is concentrated and the residue containing D-tert-leucine is racemized using a base to obtain DL-tertleucine.

7. The process of claim 1 wherein the polar solvent is water.

8. A process for the preparation of enantiomerically pure tertiary-leucine which is D-tert-leucine by resolution of (DL)-tertiary-leucine by forming a diastereomeric salt using a resolving agent selected from optically active tartaric acid derivatives, comprising:
   (a) dissolving (DL)-tent-leucine in a polar solvent and treating it with dibenzoyl-d-tartaric acid to create a suspension,
   (b) filtering the suspension to obtain selectively L-tert-leucine dibenzoyl-d-tartrate salt, and
   (c) concentrating the filtrate to obtain D-tert-leucine.

9. The process of claim 3 wherein the barium compound is barium hydroxide.

10. The process of claim 5 wherein the non-basis acid scavenger is epichlorohydrin.

11. The process of claim 5 wherein the non-basic acid scavenger is an epoxide.

12. The process of claim 6 wherein the base is ammonium hydroxide.

13. The process of claim 8 wherein the polar solvent is water.

* * * * *